(12) United States Patent
Yu

(10) Patent No.: US 6,723,500 B2
(45) Date of Patent: Apr. 20, 2004

(54) TEST STRIPS HAVING REACTION ZONES AND CHANNELS DEFINED BY A THERMALLY TRANSFERRED HYDROPHOBIC BARRIER

(75) Inventor: Yeung Siu Yu, Pleasanton, CA (US)

(73) Assignee: LifeScan, Inc., Milpitas, CA (US)

( * ) Notice: Subject to any disclaimer, the term of this patent is extended or adjusted under 35 U.S.C. 154(b) by 0 days.

(21) Appl. No.: 10/011,000

(22) Filed: Dec. 5, 2001

(65) Prior Publication Data

US 2003/0104510 A1 Jun. 5, 2003

(51) Int. Cl.$^7$ ................................................. C12Q 1/00
(52) U.S. Cl. ................................ 435/4; 435/14; 422/58
(58) Field of Search ............................. 435/4, 14, 25, 435/287.8, 805, 970, 973; 422/55–60, 947; 436/169, 170

(56) References Cited

U.S. PATENT DOCUMENTS

| | | | |
|---|---|---|---|
| 3,001,915 A | | 9/1961 | Fonner et al. |
| 3,127,281 A | | 3/1964 | Meyer |
| 3,785,929 A | | 1/1974 | Kronish et al. |
| 4,301,115 A | | 11/1981 | Rapkin et al. |
| 4,618,475 A | * | 10/1986 | Wang .......................... 422/56 |
| 4,622,207 A | * | 11/1986 | Wang .......................... 422/56 |
| 4,673,657 A | * | 6/1987 | Christian ..................... 436/501 |
| 4,687,529 A | | 8/1987 | Wang |
| 4,861,711 A | * | 8/1989 | Friesen et al. .................. 436/7 |
| 4,877,745 A | * | 10/1989 | Hayes et al. ................. 436/166 |
| 4,960,565 A | * | 10/1990 | Shurben ....................... 422/61 |
| 4,960,691 A | * | 10/1990 | Gordon et al. .................. 435/6 |
| 5,073,484 A | * | 12/1991 | Swanson et al. ............. 435/7.92 |
| 5,208,163 A | | 5/1993 | Charlton et al. |
| 5,240,844 A | * | 8/1993 | Wie et al. ................... 435/7.92 |
| 5,338,688 A | * | 8/1994 | Deeg et al. .................. 436/180 |
| 5,356,782 A | * | 10/1994 | Moorman et al. ............ 435/7.9 |
| 5,451,350 A | | 9/1995 | Macho et al. |
| 5,476,330 A | | 12/1995 | Inoue et al. |
| 5,563,042 A | | 10/1996 | Phillips et al. |
| 5,607,565 A | | 3/1997 | Azarnia et al. |
| D381,591 S | | 7/1997 | Rice et al. |
| 5,719,034 A | | 2/1998 | Kiser et al. |
| 5,820,284 A | | 10/1998 | Owada et al. |
| 5,830,170 A | | 11/1998 | Whiteman et al. |
| 5,843,691 A | | 12/1998 | Douglas et al. |
| 5,935,520 A | * | 8/1999 | Fujisaki et al. ................ 422/58 |
| 5,951,836 A | | 9/1999 | McAleer et al. |
| 5,952,173 A | * | 9/1999 | Hansmann et al. ............ 435/6 |
| 6,003,980 A | | 12/1999 | Sheinman et al. |
| 6,121,050 A | * | 9/2000 | Han .............................. 436/95 |
| 6,194,220 B1 | * | 2/2001 | Malick et al. ............... 436/514 |
| 6,228,660 B1 | | 5/2001 | May et al. |
| 6,241,862 B1 | | 6/2001 | McAleer et al. |
| 6,251,083 B1 | | 6/2001 | Yum et al. |
| 6,368,876 B1 | * | 4/2002 | Huang et al. ................ 436/518 |
| 6,403,384 B1 | * | 6/2002 | Lea ............................. 436/518 |
| 6,410,341 B1 | * | 6/2002 | Freitag et al. ............... 436/514 |
| 6,451,619 B1 | * | 9/2002 | Catt et al. .................... 436/514 |
| 6,455,001 B1 | * | 9/2002 | Knappe et al. ................ 422/56 |
| 2002/0138222 A1 | * | 9/2002 | Carpenter et al. ........... 702/104 |
| 2002/0168692 A1 | * | 11/2002 | Cass .......................... 435/7.9 |

FOREIGN PATENT DOCUMENTS

| | | | |
|---|---|---|---|
| DE | 40677 | * | 1/1964 |
| WO | WO 00/58730 | * | 10/2000 |

* cited by examiner

*Primary Examiner*—Ralph Gitomer
(74) *Attorney, Agent, or Firm*—Carol M. LaSalle; Bozicevic, Field & Francis, LLP (57) ABSTRACT

Test strips, and methods for their manufacture and use in the determination of the concentration of at least one analyte in a physiological sample are provided. The subject test strips have a plurality of reaction zones defined by a hydrophobic barrier. The reagent compositions present in each reaction zone may be the same or different. In addition, each reaction zone may have a separate fluid channel, or two or more of the reaction zones may have separate channels that merge into a single channel. In use, sample is applied to a subject test strip, a signal is detected and then related to the amount of analyte in the sample. Also provided are methods for manufacturing the subject test strips using thermal transfer technology to apply the hydrophobic barrier. Finally, kits are provided for use in practicing the subject methods.

14 Claims, 5 Drawing Sheets

TEST STRIPS HAVING REACTION ZONES AND CHANNELS DEFINED BY A THERMALLY TRANSFERRED HYDROPHOBIC BARRIER

FIELD OF THE INVENTION

The field of this invention is analyte determination, particularly blood analyte determination and more particularly blood glucose determination.

BACKGROUND OF THE INVENTION

Analyte concentration determination in physiological samples is of ever increasing importance to today's society. Such assays find use in a variety of application settings, including clinical laboratory testing, home testing, etc., where the results of such testing play a prominent role in the diagnosis and management of a variety of disease conditions. Analytes of interest include glucose for diabetes management, cholesterol for monitoring cardiovascular conditions, and the like. In response to this growing importance of analyte concentration characterization, a variety of analyte concentration characterization protocols and devices for both clinical and home testing have been developed.

One type of device that is employed for analyte concentration determination is a test strip. Oftentimes, such a test strip is based on the production of hydrogen peroxide and the subsequent detection thereof. Analyte concentrations that may be determined using such assays include: cholesterol, triglycerides, glucose, ethanol and lactic acid. For example, glucose is quantitated using such assays by first oxidizing glucose with glucose oxidase to produce gluconic acid and hydrogen peroxide in a reaction area or zone of the test strip. The resultant hydrogen peroxide, in conjunction with a peroxidase, causes the conversion of one or more organic substrates, i.e., an indicator, into a chromogenic product, which product is then detected and related to the glucose concentration in the initial sample.

Oftentimes, a test strip for determining analyte concentration may be configured to include more than one reaction areas or zones, where the reaction areas include the one or more testing or reaction reagents necessary for analyte determination. Thus, it will be apparent that in the above described multi reaction area test strips it is important to segregate the reaction areas from each other so as not to contaminate the separate areas, for example with reagents or even final product from other reaction areas. This is particularly important if the reaction areas have different reagents or different concentrations of the same reagents. However, even if all of the reaction areas were to have the same reagents present in the same concentrations, it is obvious that reaction area isolation is necessary to prevent cross contamination and provide accurate, reliable and reproducible analyte determination results.

One method that has been proposed to isolate reaction areas of a multi reaction area test strip is disclosed in U.S. Pat. No. 5,843,691 to Douglas, et. al. The '691 patent teaches the creation of both non-bibulous (non absorbent) and bibulous (absorbent) areas on a test strip membrane by crushing the membrane to make it non bibulous (but still hydrophilic) everywhere except for the reaction areas, which remain bibulous. This test strip includes an intermediate layer which lies adjacent the membrane having cut outs to provide physical barriers around each reaction area. The intermediate layer barriers are needed to prevent sample located in one reaction area from moving to other reaction areas over the non-bibulous, but hydrophilic areas, thereby contaminating the other reaction areas. As such, the intermediate layer must be precisely aligned with each reaction area so as to prevent such contamination and allow the required amount of sample to be applied to each reaction area. However, this method of compressing the membrane to create a plurality of bibulous reaction areas amongst a non bibulous background and separating the reaction areas, while effective, can be complex and costly to manufacture due to its compression step and the necessity of precisely aligning the intermediate layer with the reaction areas of the test strip.

Due to the broad applicability of analyte determination protocols, there continues to be interest in the identification of new devices and methods in this area. Of particular interest would be the development of such devices and methods of use thereof which are simple to use, accurate, precise and easy and low cost to manufacture.

SUMMARY OF THE INVENTION

Test strips and methods for their manufacture and use in the determination of the concentration of at least one analyte in a physiological sample are provided. The subject test strips have a plurality of reaction zones defined by a hydrophobic barrier. The reagent compositions present in each reaction zone may be the same or different. In addition, each reaction zone may have a separate fluid channel, or two or more of the reaction zones may have separate channels that merge into a single channel. In use, sample is applied to a subject test strip, a signal is detected and then related to the amount of analyte in the sample. Also provided are methods for manufacturing the subject test strips using thermal transfer technology to apply the hydrophobic barrier. Finally, kits are provided for use in practicing the subject methods.

DETAILED DESCRIPTION OF THE INVENTION

Test strips, and methods for their manufacture and use in the determination of the concentration of at least one analyte in a physiological sample are provided. The subject test strips have a plurality of reaction zones defined by a hydrophobic barrier. The reagent compositions present in each reaction zone may be the same or different. In addition, each reaction zone may have a separate fluid channel, or two or more of the reaction zones may have separate channels that merge into a single channel. In use, sample is applied to a subject test strip, a signal is detected and then related to the amount of analyte in the sample. Also provided are methods for manufacturing the subject test strips using thermal transfer technology to apply the hydrophobic barrier. Finally, kits are provided for use in practicing the subject methods.

Before the present invention is described, it is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an", and "the" include plural referents unless the context clearly dictates otherwise. Thus, for example, reference to "a test strip" includes a plurality of such test strips and reference to "the device" includes reference to one or more devices and equivalents thereof known to those skilled in the art, and so forth.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Devices

As summarized, test strips are provided that have separate, isolated reaction zones or areas. Specifically, the test strips are generally characterized by having a plurality of reaction zones defined by hydrophobic areas associated with a porous matrix. The reaction zones include a reagent composition that typically has one or more members of a signal producing system such as an analyte oxidation signal producing system.

Any convenient testing system or signal producing system may be used with the present invention, where the particular system will depend on a variety of factors such as the analyte of interest, the type of assay system used, i.e., colorimetric, electrochemical, radiometric, and the like. By way of example and not limitation, exemplary signal producing systems useful with the subject invention will now be described.

As mentioned above, in addition to the porous matrix, the subject test strips include one or more members of a signal producing system which produces a detectable product in response to the presence of analyte, which detectable product can be used to derive the amount of analyte present in the assayed sample. In the subject test strips, the one or more members of the signal producing system are associated, e.g. covalently or non-covalently attached to, at least a portion of (i.e., the detection region or reaction zones) the porous matrix, and in many embodiments to substantially all of the porous matrix.

In certain embodiments, e.g., where glucose is the analyte of interest, the signal producing system is an analyte oxidation signal producing system. By analyte oxidation signal producing system is meant that in generating the detectable signal from which the analyte concentration in the sample is derived, the analyte is oxidized by a suitable enzyme to produce an oxidized form of the analyte and a corresponding or proportional amount of hydrogen peroxide. The hydrogen peroxide is then employed, in turn, to generate the detectable product from one or more indicator compounds, where the amount of detectable product generated by the signal measuring system, i.e. the signal, is then related to the amount of analyte in the initial sample. As such, the analyte oxidation signal producing systems present in the embodiments of the subject test strips using such systems are also correctly characterized as hydrogen peroxide based signal producing systems.

As indicated above, the hydrogen peroxide based signal producing systems include an enzyme that oxidizes the analyte and produces a corresponding amount of hydrogen peroxide, where by corresponding amount is meant that the amount of hydrogen peroxide that is produced is proportional to the amount of analyte present in the sample. The specific nature of this first enzyme necessarily depends on the nature of the analyte being assayed but is generally an oxidase. As such, the first enzyme may be: glucose oxidase (where the analyte is glucose); cholesterol oxidase (where the analyte is cholesterol); alcohol oxidase (where the analyte is alcohol); lactate oxidase (where the analyte is lactate) and the like. Other oxidizing enzymes for use with these and other analytes of interest are known to those of skill in the art and may also be employed. In those embodiments where the reagent test strip is designed for the detection of glucose concentration, the first enzyme is glucose oxidase. The glucose oxidase may be obtained from any convenient source, e.g. a naturally occurring source such as *Aspergillus niger* or Penicillum, or recombinantly produced.

The second enzyme of the signal producing system is an enzyme that catalyzes the conversion of one or more indicator compounds into a detectable product in the presence of hydrogen peroxide, where the amount of detectable product that is produced by this reaction is proportional to the amount of hydrogen peroxide that is present. This second enzyme is generally a peroxidase, where suitable peroxidases include: horseradish peroxidase (HRP), soy peroxidase, recombinantly produced peroxidase and synthetic analogs having peroxidative activity and the like. See e.g., Y. Ci, F. Wang; Analytica Chimica Acta, 233 (1990), 299-302.

The indicator compound or compounds, e.g. substrates, are ones that are either formed or decomposed by the hydrogen peroxide in the presence of the peroxidase to produce an indicator dye that absorbs light in a predetermined wavelength range. Preferably the indicator dye absorbs strongly at a wavelength different from that at which the sample or the testing reagent absorbs strongly. The oxidized form of the indicator may be a colored, faintly-colored, or colorless final product that evidences a change in color of the testing side of the membrane. That is to say, the testing reagent can indicate the presence of glucose in a sample by a colored area being bleached or, alternatively, by a colorless area developing color.

Indicator compounds that are useful in the present invention include both one- and two-component chromogenic substrates. One-component systems include aromatic amines, aromatic alcohols, azines, and benzidines, such as tetramethyl benzidine-HCl. Suitable two-component systems include those in which one component is MBTH, an MBTH derivative (see for example those disclosed in U.S. patent application Ser. No. 08/302,575, incorporated herein by reference), or 4-aminoantipyrine and the other component is an aromatic amine, aromatic alcohol, conjugated amine, conjugated alcohol or aromatic or aliphatic aldehyde. Exemplary two-component systems are 3-methyl-2-benzothiazolinone hydrazone hydrochloride (MBTH) combined with 3-dimethylaminobenzoic acid (DMAB); MBTH combined with 3,5-dichloro-2-hydroxybenzene-sulfonic acid (DCHBS); and 3-methyl-2-benzothiazolinonehydrazone N-sulfonyl benzenesulfonate monosodium (MBTHSB) combined with 8-anilino-1 naphthalene sulfonic acid ammonium (ANS). In certain embodiments, the dye couple MBTHSB-ANS is preferred.

In yet other embodiments, signal producing systems that produce a fluorescent detectable product (or detectable non-fluorescent substance, e.g. in a fluorescent background) may be employed, such as those described in: Kiyoshi Zaitsu, Yosuke Ohkura: New fluorogenic substrates for Horseradish Peroxidase: rapid and sensitive assay for hydrogen peroxide and the Peroxidase. Analytical Biochemistry (1980) 109, 109–113.

Generally, for colorimetric assays, the sample is allowed to react with the members of the signal producing system to produce a detectable product that is present in an amount proportional to the initial amount present in the sample. The amount of detectable product, i.e., signal produced by the signal producing system, is then determined and related to the amount of analyte in the initial sample. As described, in certain embodiments, automated meters, i.e., optical meters, that perform the above mentioned detection and relation steps are employed. The above described reaction, detection and relating steps, as well as instruments for performing the same, are further described in U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference.

In certain embodiments, the subject test strips or rather the testing reagent composition may further include a component for inhibiting the component that detects the hydrogen peroxide and may optionally further include a separating component which causes solids, such as red blood cells, to become entrapped in the matrix, effectively removing the solids from the biological fluid. Each of these two components will now be described in greater detail.

As described above, the optional inhibiting component retards the reaction between the hydrogen peroxide and the indicator, for example by reducing the hydrogen peroxide or by reducing the oxidized indicator. In principle there are several different modes of operation for an inhibitor. First, the inhibitor could compete with the indicator and thereby slow the rate at which the color change takes place in the indicator. Second, the inhibitor could be non-competitive, so that substantially all the inhibitor is consumed before any substantial color change takes place in the indicator. Other modes of inhibitor operation are also possible. In many embodiments, inhibitors of the present invention are non-competitive.

Among the range of suitable inhibitors are 2,3,4-trihydroxybenzoic acid; propyl gallate; 3,4 dihydroxy cinnamic acid; 3,4 dihydroxy benzaldehyde; gallic acid; 5,6-diaminouracil; ascorbic acid; and isoascorbic acid. If ascorbic acid is used, however, ascorbic acid oxidizes in solution and must be stabilized in order to permit the reagent to be coated. Suitable stabilizers are primary alcohols, such as ethyl, methyl, or propyl alcohol, where ethyl alcohol is of particular interest, particularly concentrated solutions; i.e., solutions of 50% or more ethanol.

Although an anisotropic membrane, if used, filters out red blood cells and holds them away from the testing side of the matrix, optionally a separating component may be used, as mentioned above. The separating component should be capable of producing a relatively clear, colorless fluid from fluid containing red blood cells, e.g., whole blood, by sequestering red blood cells in the matrix. Separating components for use in the instant invention include but are not limited to polyethylene glycol, poly (methylvinyl ether/maleic)anhydride, polypropylene glycol, polystyrene sulfonic acid, polyacrylic acid, polyvinyl alcohol, and polyvinyl sulfonic acid at a pH of between about 4.0–8.0. Such separating components are present in the matrix in amounts that will vary depending upon their charge and molecular weight, the other components imbedded in the matrix, the matrix pH and pore size, and the residual moisture of the matrix after drying. Such parameters are readily determinable by one skilled in the art. For example, when polypropylene glycol is employed as the separating component (e.g., PPG-410 from BASF, Wyandotte, Mich.), it is usually present at about 2–30% weight to volume (w/v), and more preferably 8–10% w/v. Other separating components can also be employed in a concentration of about 2–30% w/v. The polymeric separating components may be impregnated or imbedded in the matrix or cast in the membrane during manufacture. Some water soluble salts can also effect blood separation. Among salts suitable for separating blood components are citrates, formates, and sulfates, as well as certain acids, such as amino acids, citric acid, phytic acid, and malic acid (See, e.g., U.S. Pat. No. 3,552,928, issued Jan. 5, 1971, to M. C. Fetter). An advantage of including the separating component is that with solids, such as red blood cells, substantially removed from the biological fluid, there is less background color at the test site to obscure a change in coloration produced by the testing reagent.

Other components may be imbedded into the matrix to enhance the coloration and readability of the reagent strips and to preserve the uniformity and integrity of the matrix. For example, the testing reagent may include salts and/or buffers to aid in the separation of the dye in the matrix. Such buffers may contain for example, citrate, present in solution at from about 0.01M to about 1.0M, and preferably at about 0.1M. Other buffers may also be employed.

Compounds that make the matrix hydrophilic or compounds that can act as stabilizers, such as hydrolyzed proteins, may also be employed. Such compounds include but are not limited to for example bovine serum albumin, polypeptides and the low molecular weight protein available as Crotein SPA (CRODA, Inc. New York, N.Y.). Such compounds are used at concentrations of for example about 1 mg/mL to about 100 mg/mL. In the case of Crotein, about 30 mg/mL is preferred.

Other stabilizers and preservatives may also be included in the coating for the matrix. For example ethylene diamine tetraacetic acid (EDTA), diethylene triamine pentaacetic acid (DTPA) and related compounds may be employed, for example, at concentrations of about 0.01 mg/mL to about 10 mg/mL. Among the purposes of the preservatives is to help to stabilize the inhibitor.

Some of the indicators may have an undesirable tendency to migrate in the matrix. When such an indicator is used, an ion pairing agent is included to prevent such migration. For example, the polyethylene glycol derivatives commercially available as Polyquart (H) (Henkel, Inc., Ambler, Pa.) are particularly useful for their ability to facilitate ion pairing between the indicator and other matrix substituents.

When the presence of an analyte is indicated by color formation (e.g., MBTHSB-ANS), surfactants may be added to brighten the color and enhance the contrast with the uncolored surround.

Organic solvents may also be employed in the practice of this invention and may be included in the formulation of the testing reagent for the matrix, provided, of course, that they are compatible with the matrix and testing reagent compositions. Potentially suitable organic solvents include chloroform, acetone, alcohols, methylene chloride, diethyl and petroleum ethers, acetonitriles, and mixtures thereof. In the practice of the present invention, 70% ethanol in water is of particular interest.

Figure 2:
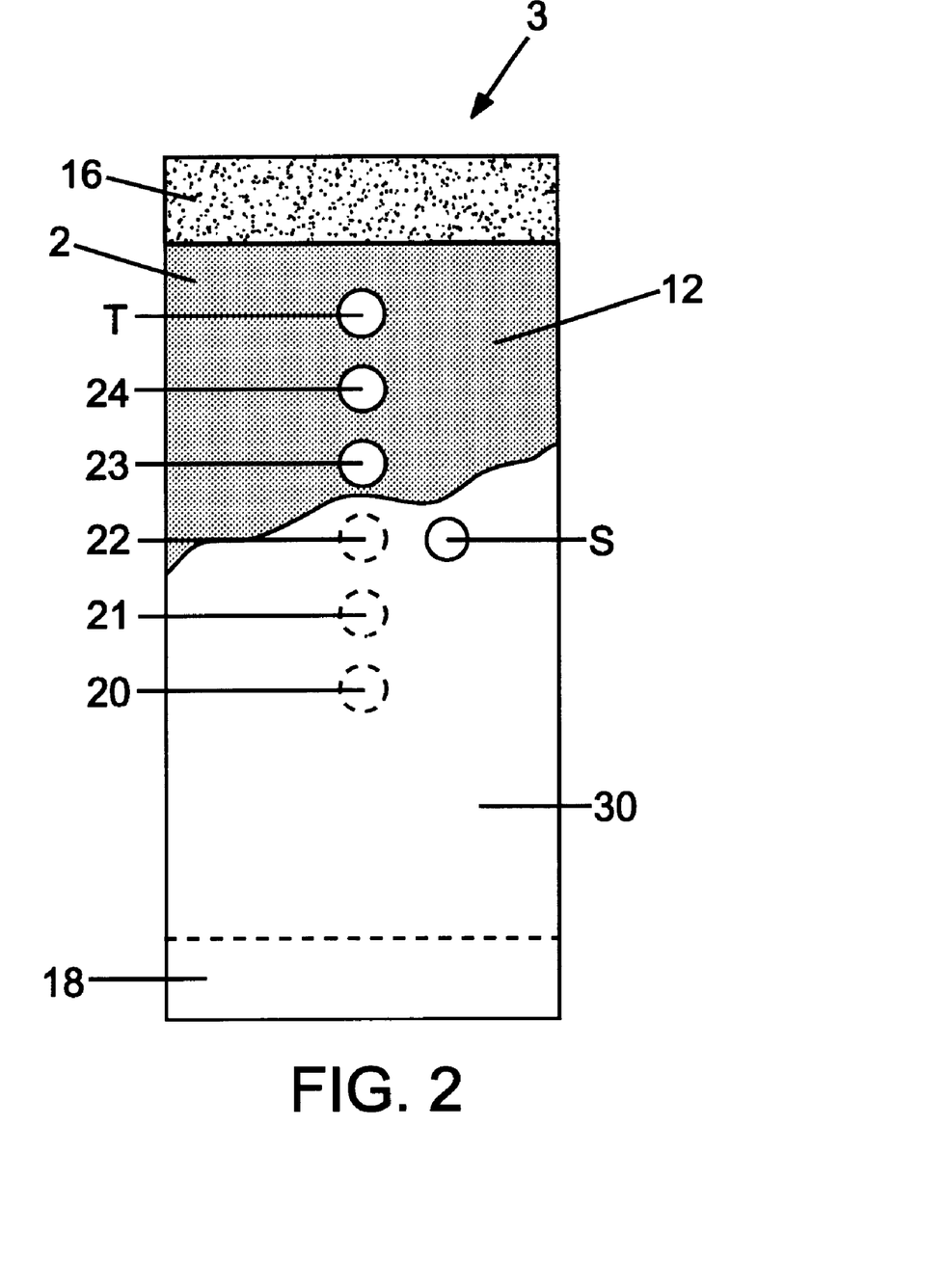
FIG. 2 provides a bottom plan view, in partial cutaway, of an exemplary test strip.

As the subject test strips have a plurality of reaction zones defined by hydrophobic areas, the reaction zones may be the same or different, where the difference in reaction zones may be attributed to the concentration of the testing system in a reaction zone, i.e., the concentration of one or more components of the testing system, the type of testing system in a reaction zone, i.e., the analyte to be determined (one or more reaction areas may determine the presence and/or concentration of analytes different from analytes determined in other reaction areas), and the like. The subject test strips generally include at least two reaction zones, where the number of reaction zones in the test strips according to the subject invention generally ranges from about 2 to 25, usually from about 2 to 15 and more usually from about 2 to 10. While the reaction zones may, in general, be arranged in any convenient manner on the test strip, in many embodiments they are arranged in a row, i.e., one next to another, down the center of the test strip, as shown in FIG. 2. In further describing the subject invention, the various components and configurations of the subject test strips will now be described in greater detail.

The matrix or membrane (herein used interchangeably) that is employed in the subject test strips is an inert porous matrix which provides a support for the various members of the signal producing system, described below, as well as the light absorbing or chromogenic product produced by the signal producing system, i.e., the indicator. The inert porous matrix is configured to provide a location for the physiological sample, e.g., blood, application and a location for the detection of the light-absorbing product produced by the indicator of the signal producing system. As such, the inert porous matrix is one that is permissive of aqueous fluid flow through it and provides sufficient void space for the chemical reactions of the signal producing system to take place. A number of different porous matrices have been developed for use in various analyte detection assays, which matrices may differ in terms of materials, pore sizes, dimensions and the like, where representative matrices include those described in U.S. Pat. Nos.: 4,734,360; 4,900,666; 4,935, 346; 5,059,394; 5,304,468; 5,306,623; 5,418,142; 5,426, 032; 5,515,170; 5,526,120; 5,563,042; 5,620,863; 5,753, 429; 5,573,452; 5,780,304; 5,789,255; 5,843,691; 5,846, 486; 5,968,836 and 5,972,294; the disclosures of which are herein incorporated by reference. In principle, the nature of the porous matrix is not critical to the subject test strips and therefore is chosen with respect to other factors, including the nature of the instrument which is used to read the test strip, convenience and the like. As such, the dimensions and porosity of the matrix may vary greatly. Typically, a matrix of less than about 200 microns in thickness, usually from about 115 to 155 microns in thickness and more usually from about 130 to 140 microns in thickness is employed, where the matrix may or may not have a porosity gradient, e.g. with larger pores near or at the sample application region and smaller pores at the detection region. In certain embodiments, the length of the matrix typically ranges from about 6 mm to about 65 mm, usually from about 10 mm to about 50 mm and more usually from about 10 mm to about 40 mm and the width of the matrix typically ranges from about 5 mm to about 20 mm, usually from about 7 mm to about 20 mm and more usually from about 7 mm to about 15 mm. Materials from which the matrix may be fabricated vary, and include, but are not limited to, polymers, e.g. polysulfone, polyamides, cellulose or absorbent paper, and the like, where the material may or may not be functionalized to provide for covalent or non-covalent attachment of the various members of the signal producing system.

As described above, a plurality of reaction zones are present on the test strip and more specifically the matrix of the test strip. That is, the matrix includes more than one reaction zone, where the reaction zones may be the same or different, i.e., at least two of the reaction zones may differ. In certain embodiments of the invention, the testing reagent system is the same in all the disparate reaction zones of the test strip, e.g., in multi-use test strips. In other embodiments, e.g., where the strip is employed to simultaneously assay for a panel or plurality of different analytes, the reagent composition will differ among the disparate reaction zones. In other words, at least two different reagent compositions will be present in different reaction zones of the test strip, where the number of different reagent compositions may be as great as the number of different reaction zones of the test strip. In certain other embodiments, the reagent composition may be the same in all or substantially all the reaction zones (i.e., the reaction zones assay for the same analyte), but the composition in adjoining reaction zones may increase or decrease stepwise, in inhibitor concentration. As described, in the reaction zone, the testing reagents react with the analyte of interest, e.g., glucose, to produce a detectable product, provided that the glucose concentration is large enough to overcome the inhibitor level (if used) in that particular reaction zone. Thus, each succeeding reaction zone, if made of increasing amounts of inhibitor, requires a greater glucose concentration in the sample to cause a detectable product. Still further, one or more of the reaction areas may include a control solution for verifying the integrity of the test. Yet further, one or more reaction zones may be adapted to serve as a timer to indicate that enough time has elapsed for the testing reagents to react with the analyte in each of the reaction zones (see for example, U.S. Pat. No. 5,843,691, the disclosure of which is herein incorporated by reference).

Regardless of whether the reaction zones are the same or different, as described above, the matrix also includes a hydrophobic composition or barrier, where such a hydrophobic composition is positioned on the matrix to define the reaction zones, that is to define the areas of the reaction zones. Specifically, the reaction zones positioned on the matrix are bounded by a hydrophobic composition which creates a barrier, i.e., a hydrophobic barrier or area around each reaction zone. More specifically, the reaction zones are hydrophilic and bibulous, where the areas of the matrix surrounding the reaction zones are hydrophobic. In many embodiments, the entire surface of the matrix, excluding the reaction zones, includes the hydrophobic composition. The hydrophobic area may be a layer or coating of hydrophobic composition on the surface of the matrix or may be integrated throughout the matrix in the area of the hydrophobic composition.

A variety of hydrophobic compositions may be used to create the hydrophobic area on the matrix, where suitable compositions won't adversely interfere with the analyte determination reaction in the reaction zones. For example, representative hydrophobic compositions include, but are not limited to, hydrophobic inks such as commercially available hydrophobic ink available by Alps Electric Co., Ltd., of Tokyo, Japan. In those embodiments where the hydrophobic composition is a layer or coating, typically, the thickness of the hydrophobic composition ranges from about 1 mm to about 20 mm, usually from about 3 mm to about 15 mm and more usually from about 5 mm to about 11 mm. In many embodiments, the hydrophobic composition will be one which is deposited on the surface of the matrix using thermal transfer technology, as will be described in greater detail below.

In addition to the reagent-containing matrix, the strip of the present invention includes a bottom layer that supports the matrix. The bottom layer may be of a material that is sufficiently rigid to be inserted into the meter without undue bending or kinking. In many embodiments, the support or bottom member is made of material such as polyolefins, e.g., polyethylene or polypropylene, polystyrene or polyesters, such as Film 9962, available from 3M, St. Paul, Minn. The thickness of such a bottom layer generally ranges from about 0.05 mm to 0.2 mm. In certain embodiments, a surface of the bottom layer is hydrophilic to facilitate sample transport, i.e., at least the surface facing the matrix is hydrophilic to facilitate sample advancement to the reaction zones. However, the surface does not need to be hydrophilic.

The bottom layer typically has one or more holes, through which sample may be applied to a first or sample side of the matrix and distributed to the reaction zones thereof. In certain embodiments, each reaction zone is associated with its own sample hole, where in other embodiments, one sample hole is used to apply sample to each reaction zone. If the bottom layer is generally opaque, then one or more transparent window sections may be located an appropriate distance from the sample hole, the appearance of sample in the window(s) confirming that adequate sample has been applied to the strip. The bottom layer may also include vent holes in alignment with the assay areas to facilitate filling the assay zones uniformly.

In certain embodiments of the subject invention, an intermediate layer may be present, where such an intermediate layer is positioned between the bottom layer and the matrix and, optionally, is adhered to both of them, i.e., the intermediate layer may have an adhesive or the like on both sides. The intermediate layer is typically a thermoplastic sheet, usually a polyester sheet. In one embodiment, the intermediate layer has cut-outs that guide the sample to each of the reaction zones. Notches in the intermediate layer align with the reaction zones so that each reaction zone is substantially surrounded by the walls of the intermediate layer. In another embodiment employing an intermediate layer, the intermediate layer has an elongated slot that guides the sample across the matrix surface to the reaction zones.

To complete the test strip, an optional top or upper layer may be provided, i.e., a layer may be overlaid over the testing side of the matrix, where such a top layer may have holes which align with the reaction zones. The holes make the color changes visible and also permit oxygen to reach the reaction zones. The upper layer may be of a material that is sufficiently rigid to be inserted into the meter without undue bending or kinking. In many embodiments, the support member is made of material such as polyolefins, e.g., polyethylene or polypropylene, polystyrene or polyesters, where the thickness of such a bottom layer generally ranges from about 0.05 mm to 0.2 mm.

The test strip may further include an adhesive for maintaining the test strip components in a proper configuration. For example, an adhesive may be positioned between the bottom layer and the matrix and/or the matrix and the top layer. Of course, adhesive will be limited to non reaction zones so as not to interfere with the analyte measuring reactions.

Figure 1:
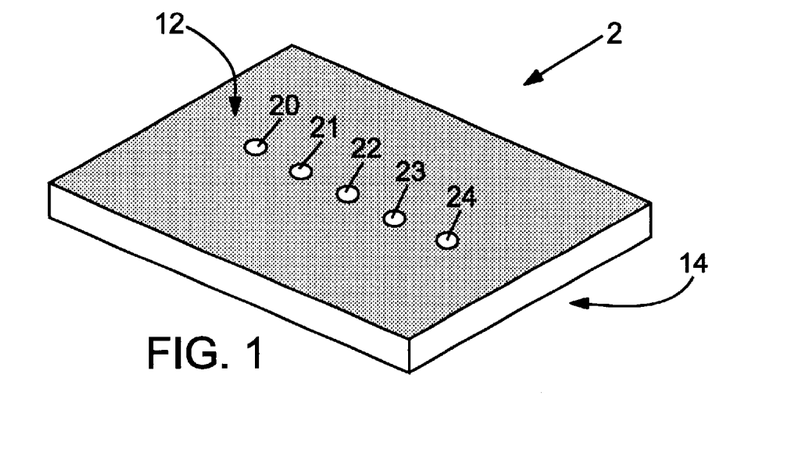
FIG. 1 provides an exemplary test strip matrix according to the present invention.

Referring now to the drawings, where like numerals represent like features or components. FIG. 1 shows an exemplary matrix 2 according to the present invention. The matrix 2 includes a sample side 12, to which the physiological fluid is applied, and a testing side 14, where the analyte is measured, e.g., by a color change detected optically or by optical measuring means, e.g., optical measuring means which measures light absorption. As mentioned above, matrix 2 typically includes pores (not shown), where such pores may have a gradient such that pore sizes are relatively large near the sample side 12 and decrease in size as testing side 14 is approached.

Figure 1A:
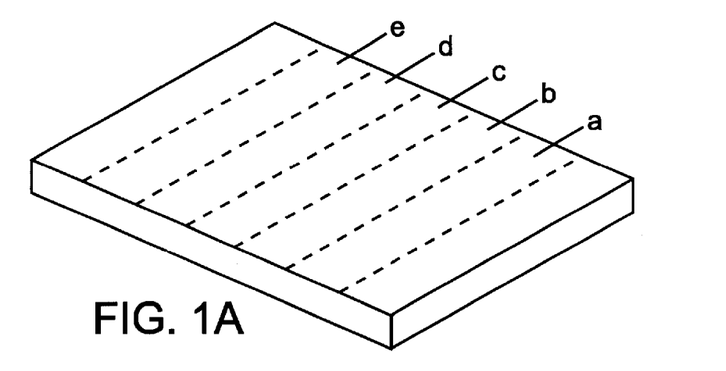
FIG. 1A shows an exemplary matrix of the present invention having testing reagent applied in parallel segments.
Figure 1B:
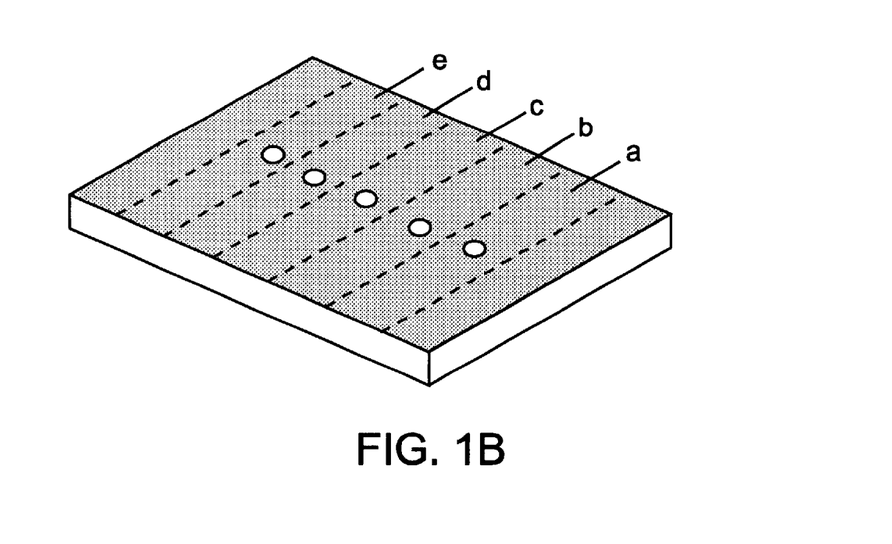
FIG. 1B shows the matrix of FIG. 1A having single reaction zones defined by hydrophobic composition in each parallel segment.

Five reaction zones 20–24 are shown in FIG. 1, each defined by a hydrophobic barrier represented by gray shading, where the reaction zones may contain the same or different testing reagents, as described above. For example, as noted above, in certain embodiments each succeeding reaction zone has more inhibitor than the preceding segment, and/or one or more may include a control solution and/or one or more may be adapted to measure an analyte different than the analyte being measured in one or more other reaction zones. Accordingly, testing reagents may be applied to the entire area of the matrix or may be applied solely to the areas of the reaction zones. For example, the matrix may be dip coated into the testing reagents or the reagents may be spotted in particular areas of the test strip. In certain embodiments of the subject invention, the testing reagent composition may be applied in parallel segments, such as parallel segments a, b, c, d and e shown in FIG. 1A. As such, a single reaction zone may be located in each of the parallel segments, each reaction zone defined by a hydrophobic barrier (shown in gray shading), i.e., a hydrophobic composition, as shown in FIG. 1B.

Regardless of whether the testing reagents encompass the entire matrix or whether the reagents are only in particular areas of the matrix, as mentioned above the matrix also includes a hydrophobic composition, as described above and shown as gray shading in the Figures. Thus, as seen in FIG. 1, the hydrophobic composition is positioned or located around the reaction zones of the matrix so as to create a hydrophobic barrier around the reaction zones. That is, a hydrophobic barrier encompasses the matrix, i.e., the sample side of the matrix, substantially every place on the matrix except the reaction zones. In certain embodiments, the hydrophobic composition is positioned on the matrix as described above, with the exception of an area on the matrix for delivering sample to the reaction zones. In other words, a sample or fluid channel may be created in the hydrophobic composition so that sample may be advanced to the reaction zones of the matrix. In certain other embodiments (not shown), the hydrophobic composition may not be substantially every place on the matrix except the reaction zones, but instead may only be in areas immediately adjacent the reaction zones to define the reaction zones.

FIG. 2 is a bottom plan view, in partial cutaway, of an exemplary test strip 3 showing the sample side 12 of the matrix 2 and optional absorbent layers 16 and 18, overlaid with a bottom layer 30. As described above, a top or upper layer (not shown) may also be included on the testing side of the matrix to support the matrix and the absorbent layers. Optional absorbent layers 16 and 18 are typically positioned at the ends of the matrix to absorb excess physiological fluid. FIG. 2 shows six hydrophilic areas or areas not having hydrophobic composition, represented by five reaction zones 20–24 and a timer T, where timer T is substantially the same as the timer disclosed in U.S. Pat. No. 5,843,691, the disclosure of which is incorporated by reference. Bottom layer 30 also includes sample hole S, herein shown positioned in the center of the bottom layer, but may be positioned elsewhere as well. Sample is introduced through sample hole S and directed to the reaction zones and optional timer, with any excess being absorbed by optional absorbent layers 16 and 18. As described above, more than one sample hole may be present, e.g., there may one sample hole for each reaction zone. As mentioned above, sample advancement may be facilitated by a hydrophilic surface of the bottom layer.

As described above, sample may be advanced either by moving along a channel such as a hydrophilic channel (not shown) of the matrix or otherwise, and may be facilitated by a hydrophilic surface of the bottom layer (if a large sample size is not a concern, the capillary channel may be omitted). In certain embodiments of the invention, each reaction zone has its own distinct channel. As such, the number of different channels in these embodiments equals the number of different reaction zones of the test strip. In yet other embodiments, two or more of the channels may merge into a single channel prior to exit from the test strip, such that fluid can be introduced to two or more different reaction zones from a single sample entry hole or port. In other words, a single channel may branch into two or more sub-channels that enter different reaction zones of the test strip. The channels may be formed by the absence of a hydrophobic composition and/or may include physical grooves in the matrix. In other words, sample may be advanced to one or more reaction zones by one or more of: a sample layer surface (i.e., bottom layer surface) that is hydrophilic, cut-outs in an intermediate layer, grooves in the matrix and/or surface of the bottom layer or hydrophilic channels on the matrix itself, formed by the absence of hydrophobic composition or the addition of a hydrophobic substance.

Figure 2A:
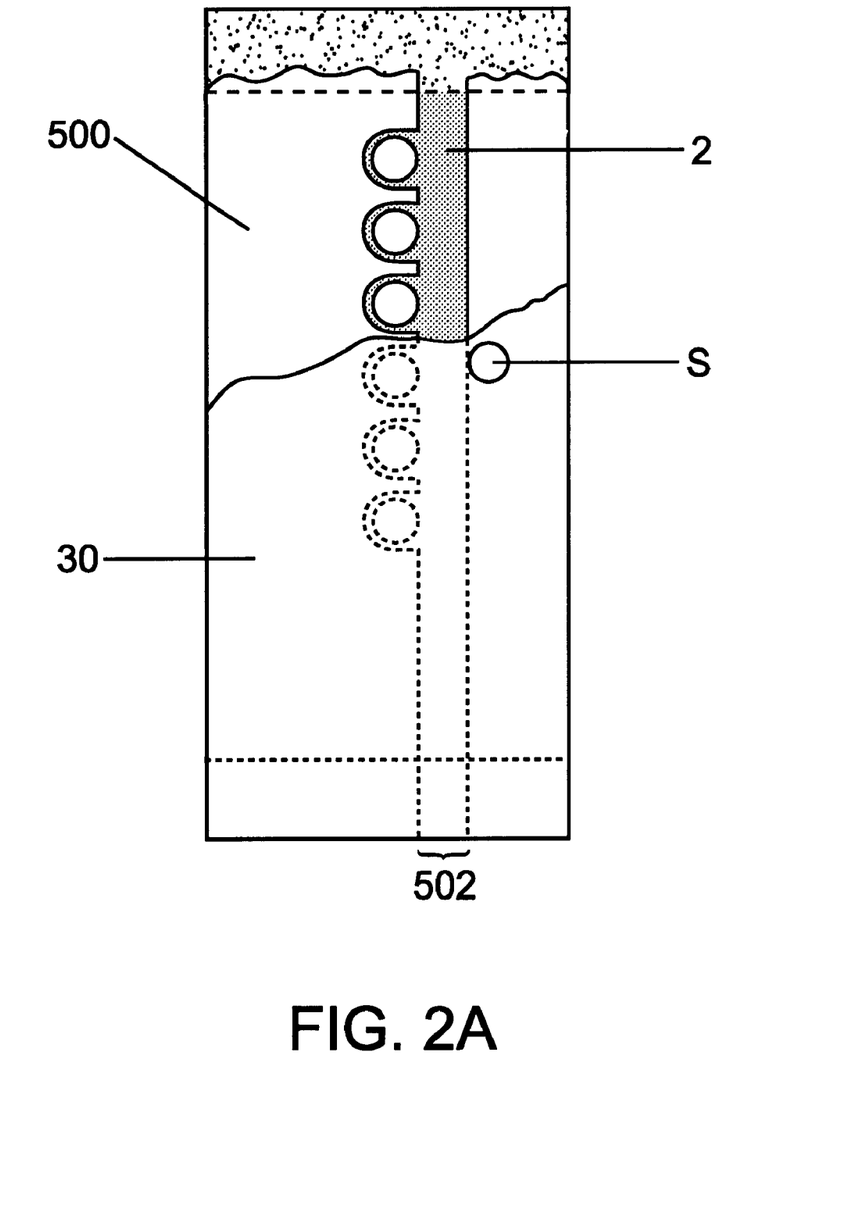
FIG. 2A provides a bottom plan view, in partial cutaway, of an exemplary test strip which is substantially the same as test strip of FIG. 2 except that it includes an intermediate layer.

FIG. 2A shows a bottom plan view, in partial cutaway, of another exemplary test strip which is substantially the same as test strip 3 of FIG. 2, except that the test strip in FIG. 2A includes an intermediate layer 500 positioned between the bottom layer 30 and the matrix 2. The intermediate layer 500 has cut-outs for notches to accommodate the reaction zones and a channel 502 which guides the sample to each reaction zone. In this particular embodiment, the matrix 2 has hydrophobic composition positioned in the channel 502, however, as noted above, this area of the matrix may be absent hydrophobic composition. Still further, the surface of the bottom layer 12 may be hydrophilic (not shown) also to facilitate sample advancement.

Bottom layer 30 may further include one or more optional clear windows (not shown) so that an individual may confirm that sufficient volume has been applied to the reaction zones.

Figure 3:
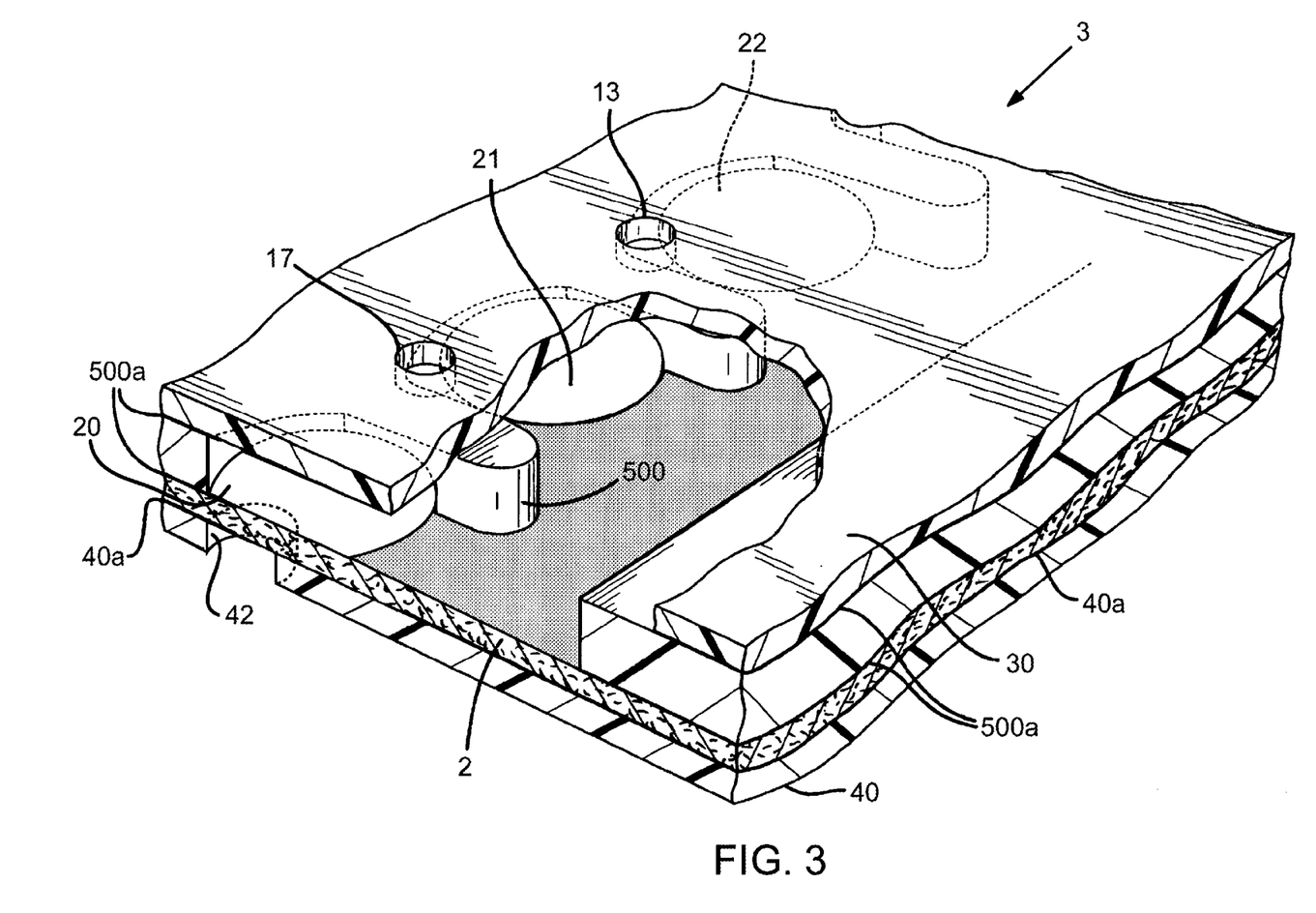
FIG. 3 provides a fragmentary perspective view of an exemplary subject test strip, such as test strip 3 of FIG. 2.

FIG. 3 is an enlarged fragmentary perspective view of an exemplary subject test strip, such as test strip 3 of FIG. 2, depicting parts of three reaction zones 20, 21 and 22, as seen through bottom layer 30, and separated by fingers of intermediate layer 500. Optional adhesive layers 500a join intermediate layer 500 to bottom layer 30 and matrix 2. The surface of bottom layer 30 facing the matrix may be hydrophilic to facilitate sample advancement to the reaction zones. As mentioned above, matrix 2 includes parts of three reaction zones 20, 21 and 22 defined by a hydrophobic composition (shown as gray shading) associated with the matrix. As shown, a hydrophobic composition defines the reaction zones such that the reaction zones are hydrophilic and include testing reagent and elsewhere on the matrix is hydrophobic. Vent holes 13 and 17 facilitate sample flow into the test strip, as mentioned above. The test strip 3 in FIG. 3 also includes optional upper layer 40, where such an upper layer may further include one or more holes such as hole 42, where such holes line-up with the reaction zones for viewing a color change in the hydrophilic reaction zones and also admit oxygen needed for the color changing reaction. Optional adhesive layer 40a is used to affix the upper layer 40 to the testing side of the matrix, where the adhesive is positioned so as not to interfere with the reaction in the reaction zones. As noted above, detecting product produced by the testing reagents and the analyte of interest and relating it to the amount of analyte may be accomplished by visual observation with the eye or automatically with a meter such as a photometric meter.

Methods of Use

Also provided by the subject invention are methods of determining the presence and/or concentration of an analyte, or panel of analytes, in a physiological sample. A variety of different analytes may be detected using the subject methods, where representative analytes include glucose, cholesterol, lactate, alcohol, and the like. In many embodiments the subject methods are employed to determine the glucose concentration in a physiological sample. While in principle, the subject methods may be used to determine the presence and/or concentration of an analyte in a variety of different physiological samples, such as urine, tears, saliva, and the like, they are particularly suited for use in determining the presence and/or concentration of an analyte in interstitial fluid, blood or blood fractions, and more particularly in whole blood.

In practicing the subject methods, the first step is to introduce a quantity of physiological fluid to at least one of the reaction zones of the test strip, where the test strip is described above. Accordingly, the sample is not absorbed or not substantially absorbed by the hydrophobic composition, i.e., the areas of the matrix having hydrophobic composition, and is instead directed to or absorbed by the reaction area(s). In many embodiments, sample is applied to all the reaction zones of the test strip at the same time. However, for multi-use test strips, i.e., strips that can be used multiple times, sample may be applied to each of the reaction zones at different times. Sample may be advanced or transferred by the hydrophilic surface of the bottom layer and/or one or more channels, where such channels do not include hydrophobic composition.

The amount of physiological sample, e.g., blood, that is introduced into the test strip may vary, but generally ranges from about 5 μl to about 25 μl, usually from about 10 μl to about 15 μl and the amount of sample introduced to each reaction area also may vary, but generally ranges from about 1 μl to about 5 μl, usually from about 2 μl to about 3 μl. The sample may be introduced into the reaction area using any convenient protocol, where the sample may be injected into the reaction area, allowed to wick into the reaction area, and the like, as may be convenient.

Following application of the sample to the one or more reaction zones, the sample is allowed to react with the members of the signal producing system to produce a detectable product that is present in an amount proportional to the initial amount present in the sample. The amount of detectable product, i.e., signal produced by the signal producing system, is then determined and related to the amount of analyte in the initial sample. The detection and relation steps can be accomplished by either direct observation with the eye or with a meter, e.g., described in U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference.

Figure 4:
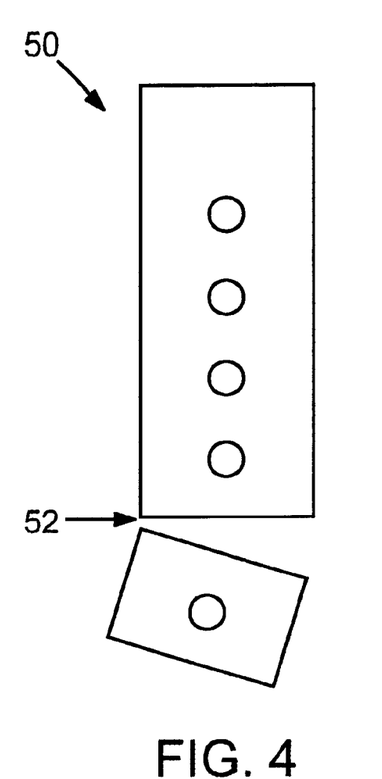
FIG. 4 provides an exemplary test strip according to the present invention.
Figure 5:
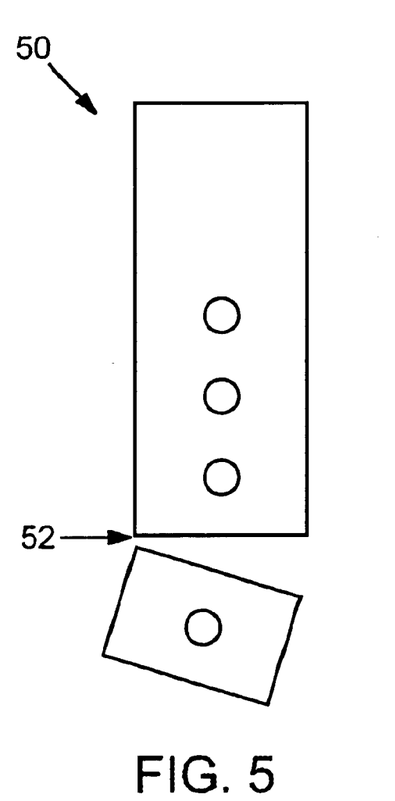
FIG. 5 provides an exemplary test strip according to the present invention.

In certain embodiments where the reaction zones of the test strips are used for different assays, where desired each used reaction zone may be separated from the remainder of the test strip, e.g., cut away from the strip, following use and prior to use of the next reaction zone. This process is illustrated in FIGS. 4 and 5, where cuts 52 are made to the strip to remove each used reaction zone prior to use of the next reaction zone.

Methods of Manufacture

Also provided my the subject invention are methods of manufacturing the subject test strips, i.e., methods of manufacturing a test strip having a matrix which includes reaction zones which are defined by hydrophobic barriers or areas. That is, hydrophobic areas, as described above, surround the reaction zones of the test strip. Thus, the subject invention provides methods of depositing or applying a hydrophobic composition, e.g., a hydrophobic ink, on the test strip matrix, where such a matrix has been described above and will not be repeated here. A feature of the subject methods is the use of a thermal head to deposit the hydrophobic composition on a surface of the matrix in a predefined pattern, where such a pattern includes areas void of the hydrophobic composition such as one or more reaction zones and/or channels for introducing sample to the reaction zones.

In certain embodiments of the subject methods, thermal transfer technology using, for example thermal transfer printers, is used to transfer a hydrophobic composition, e.g., hydrophobic ink, onto a matrix in a predetermined pattern, i.e., to create reaction zones on the matrix, where thermal transfer printers are known in the art of conventional printing and document production. As is known to those of skill in the art, thermal transfer printers typically include at least the following components: (a) a thermal head, (b) an ink ribbon, (c) a transfer means such as an intermediate transfer ribbon or belt or the like, (c) a drum or pressure roller or the like, and (d) one or more heaters. Thermal transfer printers and methods for their manufacture and use are described in a number of different U.S. patents, including: U.S. Pat. Nos. 4,544,291, 4,568,210, 4,725,853, 4,743,920, 4,770,554, 4,772,144, 4,780,729, 4,831,387, 4,887,923, 4,928,134, 4,981,381, 5,030,967 5,476,330 and 5,820,284 the disclosures of which are herein incorporated by reference.

Thermal transfer printers suitable for use with the subject invention will generally have the following characteristics. The thermal head will typically have a line head ranging from about 200 dpi to about 600 dpi. The ribbon generally includes a PET film having a thickness ranging from about 3 microns to about 5 microns as a base film and two layers formed on the base film such as a layer of wax as a release layer and a layer of hydrophobic composition layer. A variety of hydrophobic compositions may be used in the subject methods to create the hydrophobic area on the matrix, where suitable compositions won't adversely interfere with the analyte determination reaction in the reaction zones. For example, representative hydrophobic compositions include, but are not limited to, hydrophobic inks such as commercially available hydrophobic inks manufactured by Alps Electric Co., Ltd., of Tokyo, Japan. The hydrophobic composition layer will typically have a thickness ranging from about 1 mm to about 20 mm, usually from about 3 mm to about 15 mm and more usually from about 5 mm to about 11 mm and may be of any color or plurality of colors, but will typically be monochromatic or metallic (i.e., a color dye with a metallic agent such as aluminum).

In the thermal head, hydrophobic composition from the ribbon is melted by the heat generated when a signal is selectively applied to one or more heating elements to transfer the composition to the transfer means. The one or more heating element is usually capable of attaining temperatures of at least about 40° C., usually at least about 50° C. and more usually about 55° C., where the temperature is achievable by the heating element may be as high as about 70° C. or higher. A variety of thermal transfer printers are available commercially, where such devices include the MD1000 thermal printer (available from Alps Electric Co., Ltd., Tokyo, Japan).

In practicing the subject methods to deposit a hydrophobic composition onto a matrix using a thermal transfer printer, a power source is turned on and a current flows through the heaters to heat the intermediate transfer roller or the like and the drum. Also, predetermined pulses are applied intermittently to each heating element of the print head to increase the temperature of the thermal head. Typically, the print head, transfer means and drum are controlled to be maintained at about the same temperature, where such temperature usually ranges from 40° C. to about 70° C., usually from about 50° C. to about 60° C. and more usually from about 55° C. to about 58° C.

Next, the hydrophobic composition ribbon is operatively aligned with a test strip matrix upon which the hydrophobic ink is to be applied. The thermal head is pressed on the intermediate transfer roller with the ink ribbon therebetween. At about the same time, the drum is pressed on the intermediate transfer roller. At this time, the pressure of the thermal head is about 150 g/cm$^2$ to about 200 g/cm$^2$ and the pressure of the drum is about 1 Kg/cm$^2$ to about 10 Kg/cm$^2$.

After pressing is completed, the intermediate transfer roller is rotated by a motor and, at the same time, the hydrophobic composition ribbon is moved by the frictional force between the intermediate transfer roller and the ink ribbon. The drum is also rotated by the frictional force between the drum and the intermediate roller with the matrix therebetween, or the frictional force generated from the drum. The hydrophobic composition ribbon is separately wound by a motor during the printing operation.

Predetermined printing pulses are applied to the heating elements of the thermal head in parallel with the rotation of each of the parts, and the hydrophobic composition of the ribbon is melted and transferred by virtue of the heat generated from each of the heating elements in accordance with the printing signal. The melted and transferred hydrophobic composition is further rotated while maintaining a melted or semi-melted state on the transfer means by virtue of the heat of the transfer means.

The melted and transferred hydrophobic composition is re-transferred to the matrix held between the intermediate transfer roller and the drum by the contact therebetween under pressure, and the heating and insulation effect of the intermediate transfer roller and the drum.

After the hydrophobic composition has been transferred to the matrix in a predetermined pattern, i.e., transferred to form reaction areas which do not have hydrophobic composition (i.e., are defined by barriers created by the hydrophobic composition), the thermal head and drum move in directions to release pressure and the matrix, having reaction zones defined by the deposited hydrophobic composition, is separated from the drum.

As described above, the hydrophobic composition will be deposited in a predetermined pattern onto the matrix, according to a software program operatively associated with the thermal printer, where the pattern will at least include reaction zones and may also include other features such as channels, and the like and where such pattern deposition is well known in the art of art of conventional printing and document production. In other words, the hydrophobic composition, e.g., hydrophobic ink, is deposited onto the surface of the matrix in a pattern, such that there are specific areas or predetermined areas on the matrix that do not have hydrophobic composition such as areas of the reaction zones, as described above. That is, the boundaries of the reaction zones are formed or are defined by the hydrophobic composition deposited onto the surface of the matrix.

In certain embodiments of the subject methods, the hydrophobic composition is deposited over a matrix having testing reagent throughout. For example, the entire matrix may include testing reagent, but hydrophobic composition may be deposited over a portion of the testing reagent to define a smaller, particular area of testing agent, i.e., a reaction zone. In other embodiments, the area over which the hydrophobic composition is deposited will not include testing reagent. In such embodiments, testing reagent may be applied to the matrix before or after the hydrophobic composition is deposited onto the matrix, and may even be deposited at the same time, for example by the above described thermal transfer methods of application.

Kits

Also provided by the subject invention are kits for use in practicing the subject methods. The kits of the subject invention at least include a subject test strip, as described above. The subject kits may also include a plurality of such subject test strips. The subject kits may further include a means for obtaining a physiological sample. For example, where the physiological sample is blood, the subject kits may further include a means for obtaining a blood sample, such as a lance for sticking a finger, a lance actuation means, and the like. In addition, the subject kits may include a control solution, e.g., a glucose control solution that contains a standardized concentration of glucose. In certain embodiments, the subject kits, a meter instrument, as described above, for detecting a signal of a signal producing system following sample application and relating the detected signal to the amount of analyte in the sample. Finally, the kits may further include instructions for using the subject test strips for determining the presence and/or concentration of at least one analyte in a physiological sample. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

It is evident from the above description and discussion that the above described invention provides test strips having a plurality of reaction zones, where contamination of the reaction zones is substantially minimized or eliminated. The above described invention provides a number of advantages, including ease of use, precision, accuracy, reproducibility, and ease and low cost of manufacture. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A test strip for determining a concentration of at least one analyte in a physiological sample, said test strip comprising:
   a porous matrix;
   a plurality of reaction zones, wherein each of said reaction zones is defined in the porous matrix by a hydrophobic barrier deposited using thermal transfer technology;
   at least one fluid channel for delivering the physiological sample to at least one of the plurality of reaction zones, the at least one fluid channel defined by the hydrophobic barrier; and
   a reagent composition present in each of said reaction zones.

2. The test strip of claim 1, wherein said hydrophobic barrier comprises hydrophobic ink.

3. The test strip of claim 1, wherein each of said reaction zones comprise the same reagent composition.

4. The test strip of claim 1, wherein at least two of said reaction zones comprise different reagent compositions.

5. The test strip of claim 1, wherein at least two of said reaction zones are adapted for assaying for the same analyte, wherein said at least two of said reaction zones comprise different concentrations of at least one component of a testing reagent composition.

6. The test strip of claim 1, wherein at least one of said reagent compositions comprises at least one member of an analyte oxidation based signal producing system.

7. The test strip of claim 6, wherein said signal producing system further comprises an enzyme that converts at least one substrate into a chromogenic product in the presence of hydrogen peroxide.

8. The test strip of claim 7, wherein said at least one substrate comprises a dye couple.

9. The test strip of claim 7, wherein said enzyme is an oxidizing enzyme.

10. The test strip of claim 9, wherein said oxidizing enzyme is a glucose oxidizing enzyme.

11. The test strip of claim 1, wherein said analyte is glucose.

12. The test strip of claim 1, wherein said test strip is present in a meter.

13. The test strip of claim 1, wherein each of said reaction zones has its own fluid channel to provide for fluid communication between said reaction zone and the an external environment.

14. The test strip of claim 1, wherein at least two of said reaction zones have fluid channels that merge to produce a single channel to provide for fluid communication between said reaction zones and an external environment of said test strip.

* * * * *